US012622744B2

(12) United States Patent

Fry et al.

(10) Patent No.: US 12,622,744 B2

(45) Date of Patent: May 12, 2026

(54) ELECTROSURGICAL INSTRUMENT

(71) Applicant: Covidien LP, Mansfield, MA (US)

(72) Inventors: Monte S. Fry, Longmont, CO (US); Curtis M. Siebenaller, Frederick, CO (US); Michael C. Cullen, Chatham, NJ (US); William P. Verwys, East Stroudsburg, PA (US); Anthony J. Sanzari, Wood-Ridge, NJ (US); Eric B. Carmichael, Mountain Lakes, NJ (US)

(73) Assignee: Covidien LP, Mansfield, MA (US)

( * ) Notice: Subject to any disclaimer, the term of this patent is extended or adjusted under 35 U.S.C. 154(b) by 467 days.

(21) Appl. No.: 17/984,557

(22) Filed: Nov. 10, 2022

(65) Prior Publication Data

US 2023/0200888 A1    Jun. 29, 2023

Related U.S. Application Data

(60) Provisional application No. 63/278,649, filed on Nov. 12, 2021.

(51) Int. Cl.
| | |
|---|---|
| *A61B 18/12* | (2006.01) |
| *A61B 18/14* | (2006.01) |
| *A61B 17/29* | (2006.01) |
| *A61B 18/00* | (2006.01) |
| *A61B 90/00* | (2016.01) |

(52) U.S. Cl.
CPC .. *A61B 18/1447* (2013.01); *A61B 2017/2936* (2013.01); *A61B 2018/00077* (2013.01); *A61B 2018/00083* (2013.01); *A61B 2018/00101* (2013.01); *A61B 2018/0063* (2013.01); *A61B 2018/1455* (2013.01); *A61B 2090/035* (2016.02)

(58) Field of Classification Search
CPC ...... A61B 18/1447; A61B 2018/00404; A61B 2018/00607; A61B 2018/0063; A61B 2018/1455
See application file for complete search history.

(56) References Cited

U.S. PATENT DOCUMENTS

| | | | |
|---|---|---|---|
| 7,150,097 B2 | 12/2006 | Sremcich et al. | |
| 7,156,846 B2 | 1/2007 | Dycus et al. | |
| 7,491,202 B2 | 2/2009 | Odom et al. | |
| 7,686,804 B2 | 3/2010 | Johnson et al. | |

(Continued)

FOREIGN PATENT DOCUMENTS

| | | |
|---|---|---|
| AU | 2006225179 B2 | 7/2012 |
| SE | 521973 C2 | 12/2003 |

*Primary Examiner* — Daniel W Fowler

(57) ABSTRACT

An end effector assembly of a surgical instrument includes opposing first and second jaw members. A first sealing plate is positioned on the first jaw member. The first sealing plate defines a first surface facing the second jaw member. A second sealing plate is positioned on the second jaw member. The second sealing plate defines a second surface facing the first jaw member. A mesa is formed in the first sealing plate. The mesa protrudes from the first surface toward the second surface in the second position of the first and second jaw members. A material is disposed on the mesa. The mesa and the material define a stop member. The stop member maintains a gap distance between the first and second surfaces when the first and second jaw members are in the second position.

10 Claims, 7 Drawing Sheets

(56)     References Cited

U.S. PATENT DOCUMENTS

| | | | |
|---|---|---|---|
| 7,722,607 B2 | 5/2010 | Dumbauld et al. | |
| 7,731,717 B2 | 6/2010 | Odom et al. | |
| 7,766,910 B2 | 8/2010 | Hixson et al. | |
| 7,789,878 B2 | 9/2010 | Dumbauld et al. | |
| 8,298,232 B2 | 10/2012 | Unger | |
| 2004/0122423 A1 | 6/2004 | Dycus et al. | |
| 2005/0049632 A1 | 3/2005 | Inokuti et al. | |
| 2011/0270245 A1* | 11/2011 | Horner | A61B 18/1445 |
| | | | 606/41 |
| 2013/0255063 A1* | 10/2013 | Hart | A61B 18/085 |
| | | | 29/505 |
| 2015/0209103 A1* | 7/2015 | Artale | A61B 18/1445 |
| | | | 606/42 |
| 2016/0199123 A1* | 7/2016 | Thomas | A61B 18/1445 |
| | | | 264/250 |
| 2017/0209205 A1* | 7/2017 | Cho | A61B 18/1445 |
| 2017/0312019 A1* | 11/2017 | Trees | A61B 18/1442 |

* cited by examiner

ELECTROSURGICAL INSTRUMENT

CROSS REFERENCE TO RELATED APPLICATION

This application claims the benefit of U.S. Provisional Application Ser. No. 63/278,649 filed Nov. 12, 2021, the entire contents of which being incorporated by reference herein.

FIELD

The present disclosure relates to surgical instruments and, more particularly, to electrosurgical instruments for grasping, treating, and/or dividing tissue.

BACKGROUND

Instruments such as electrosurgical forceps are commonly used in open and endoscopic surgical procedures to coagulate, cauterize and seal tissue. Such forceps typically include a pair of jaw members that can be controlled by a surgeon to grasp targeted tissue, such as, e.g., a blood vessel. The jaw members may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaw members. When the adjacent layers of tissue include the walls of a blood vessel, sealing the tissue may result in hemostasis, which may facilitate the transection of the sealed tissue.

SUMMARY

Provided in accordance with aspects of the disclosure is an end effector of a surgical instrument including opposing first and second jaw members. The opposing first and second jaw members are operably coupled with each other such that at least one of the first or second jaw members is movable relative to the other of the first or second jaw members from a first position in which the first and second jaw members are disposed in spaced relation relative to one another to a second position in which the first and second jaw members cooperate to grasp tissue. A first sealing plate is positioned on the first jaw member. The first sealing plate defines a first surface facing the second jaw member. A second sealing plate is positioned on the second jaw member. The second sealing plate defines a second surface facing the first jaw member. A mesa is formed in the first sealing plate. The mesa protrudes from the first surface toward the second surface in the second position of the first and second jaw members. A material is disposed on the mesa. The mesa and the material define a stop member. The stop member maintains a gap distance between the first and second surfaces when the first and second jaw members are in the second position.

According to aspects of the disclosure, the first surface of the first sealing plate or the second surface of the second sealing plate is an electrically conductive tissue sealing surface.

According to aspects of the disclosure, a knife and knife channel are defined in at least one of the first or second jaw members. The knife is longitudinally extendable within the knife channel.

According to aspects of the disclosure, each of the first and second jaw members includes a jaw insert and an insulator configured to electrically insulate the first and second sealing plates from the jaw inserts of the first and second jaw members.

According to aspects of the disclosure, the material includes a heat-resistant ceramic material.

According to aspects of the disclosure, the material includes an electrically non-conductive plastic.

According to aspects of the disclosure, the gap distance is from about 0.001 inches to about 0.010 inches.

According to aspects of the disclosure, at least one of the first or second jaw members includes an insulator. The insulator is configured to electrically insulate the first sealing plate from the first jaw member, or the second sealing plate from the second jaw member.

According to aspects of the disclosure, the insulator is configured to guide a knife into a knife channel.

According to aspects of the disclosure, the material on the mesa is spaced apart from the first surface of the first sealing plate.

According to aspects of the disclosure, the material disposed on the mesa defines a dome shape.

According to aspects of the disclosure, the material disposed on the mesa is deposited onto the at least one mesa as a fluid.

BRIEF DESCRIPTION OF THE DRAWINGS

The above and other aspects and features of the present disclosure will become more apparent in light of the following detailed description when taken in conjunction with the accompanying drawings.

DETAILED DESCRIPTION

Figure 1:
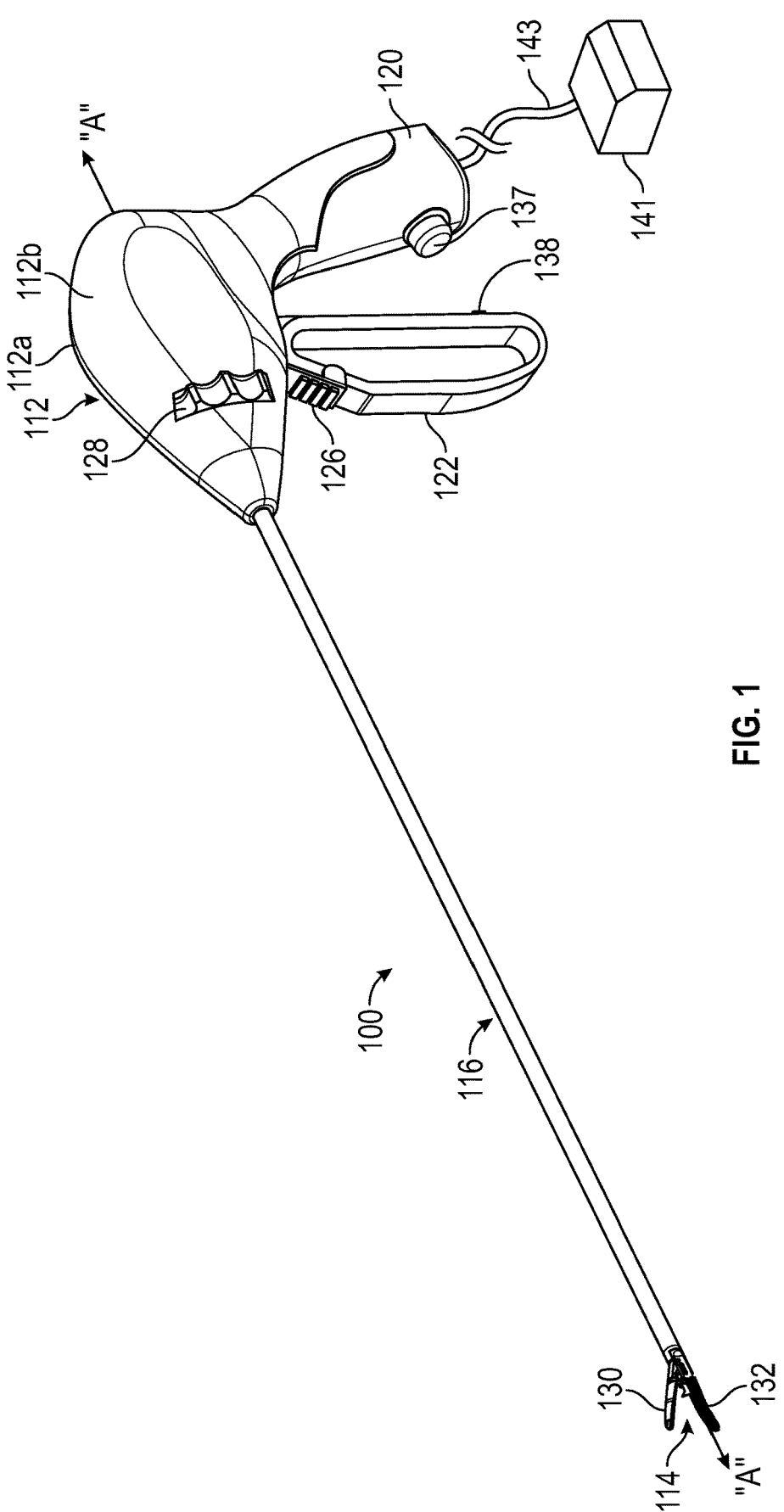
FIG. 1 is a perspective view of an electrosurgical forceps according to an aspect of the present disclosure.

As used herein, the term "distal" refers to the portion that is being described which is further from an operator (whether a human surgeon or a surgical robot), while the term "proximal" refers to the portion that is being described which is closer to an operator. Further, to the extent consistent, any of the aspects and features detailed herein may be used in conjunction with any or all of the other aspects and features detailed herein.

Descriptions of technical features or aspects of an exemplary configuration of the disclosure should typically be considered as available and applicable to other similar features or aspects in another exemplary configuration of the disclosure. Accordingly, technical features described herein according to one exemplary configuration of the disclosure may be applicable to other exemplary configurations of the disclosure, and thus duplicative descriptions may be omitted herein.

Exemplary configurations of the disclosure will be described more fully below (e.g., with reference to the accompanying drawings). Like reference numerals may refer to like elements throughout the specification and drawings.

When dispensing material to a tissue sealing plate to form a stop member, there are many variables that may affect the final shape, consistency, and fragility of the material. A mesa is a raised area to which the material is attached to the tissue sealing plate to form a stop member. By raising the mesa to a height above the sealing surface defined by the tissue sealing plate, the material forming the upper part of the stop member is more consistent and less fragile by using less dispensed material, when larger stop member heights are desired. Additionally, a larger jaw gap is achieved by using the mesa without sacrificing tissue sealing plate geometry, and the design has more flexibility through less geometry-based compromises.

The first and second surfaces described herein may operate as tissue sealing surfaces. The phrases "sealing plate" and "tissue sealing plate" may be used interchangeably herein, keeping in mind that the term "plate" as utilized herein includes any structure of a jaw member, or the entirety of the jaw member itself, that defines the tissue sealing surface without preference to any particular physical configuration except as explicitly noted otherwise.

Referring initially to FIG. 1, an electrosurgical forceps 100 generally includes a housing 112 that supports various actuators thereon for remotely controlling an end effector 114 through an elongated shaft 116. Although this configuration is typically associated with instruments for use in laparoscopic or endoscopic surgical procedures, various aspects of the present disclosure may be practiced with traditional open instruments and in connection with endoluminal procedures as well. The housing 112 is constructed of a left housing half 112a and a right housing half 112b. The left and right designation of the housing halves 112a, 112b refer to the respective directions as perceived by an operator using the forceps 100. The housing halves 112a, 112b may be constructed of sturdy plastic, and may be joined to one another by adhesives, ultrasonic welding or other suitable assembly methods.

To mechanically control the end effector 114, the housing 112 supports a stationary handle 120, a movable handle 122, a trigger 126 and a rotation knob 128. The movable handle 122 is operable to move the end effector 114 between an open configuration (see, e.g., FIG. 2A) wherein a pair of opposed jaw members 130, 132 are disposed in spaced relation relative to one another, and a closed or clamping configuration (see, e.g., FIG. 2B) wherein the jaw members 130, 132 are closer together. Approximation of the movable handle 122 with the stationary handle 120 serves to move the end effector 114 to the closed configuration and separation of the movable handle 122 from the stationary handle 120 serves to move the end effector 114 to the open configuration. The trigger 126 is operable to extend and retract a knife blade 156 (see, e.g., FIGS. 2A and 2B) through the end effector 114 when the end effector 114 is in the closed configuration. The rotation knob 128 serves to rotate the elongated shaft 116 and the end effector 114 about a longitudinal axis A-A extending through the forceps 114.

To electrically control the end effector 114, the stationary handle 120 supports a depressible button 137 thereon, which is operable by the user to initiate and terminate the delivery of electrosurgical energy to the end effector 114. The depressible button 137 is mechanically coupled to a switch disposed within the stationary handle 120 and is engageable by a button activation post 138 extending from a proximal side of the moveable handle 122 upon proximal movement of the moveable handle 122 to an actuated or proximal position. The switch 136 is in electrical communication with an electrosurgical generator 141 via suitable electrical wiring (not explicitly referenced) extending from the housing 112 through a cable 143 extending between the housing 112 and the electrosurgical generator 141. The generator 141 may include devices such as the LigaSure® Vessel Sealing Generator and the ForceTriad® Generator sold by Covidien. The cable 143 may include a connector (not shown) thereon such that the forceps 100 may be selectively coupled electrically to the generator 141.

Figures 2A, 2B:
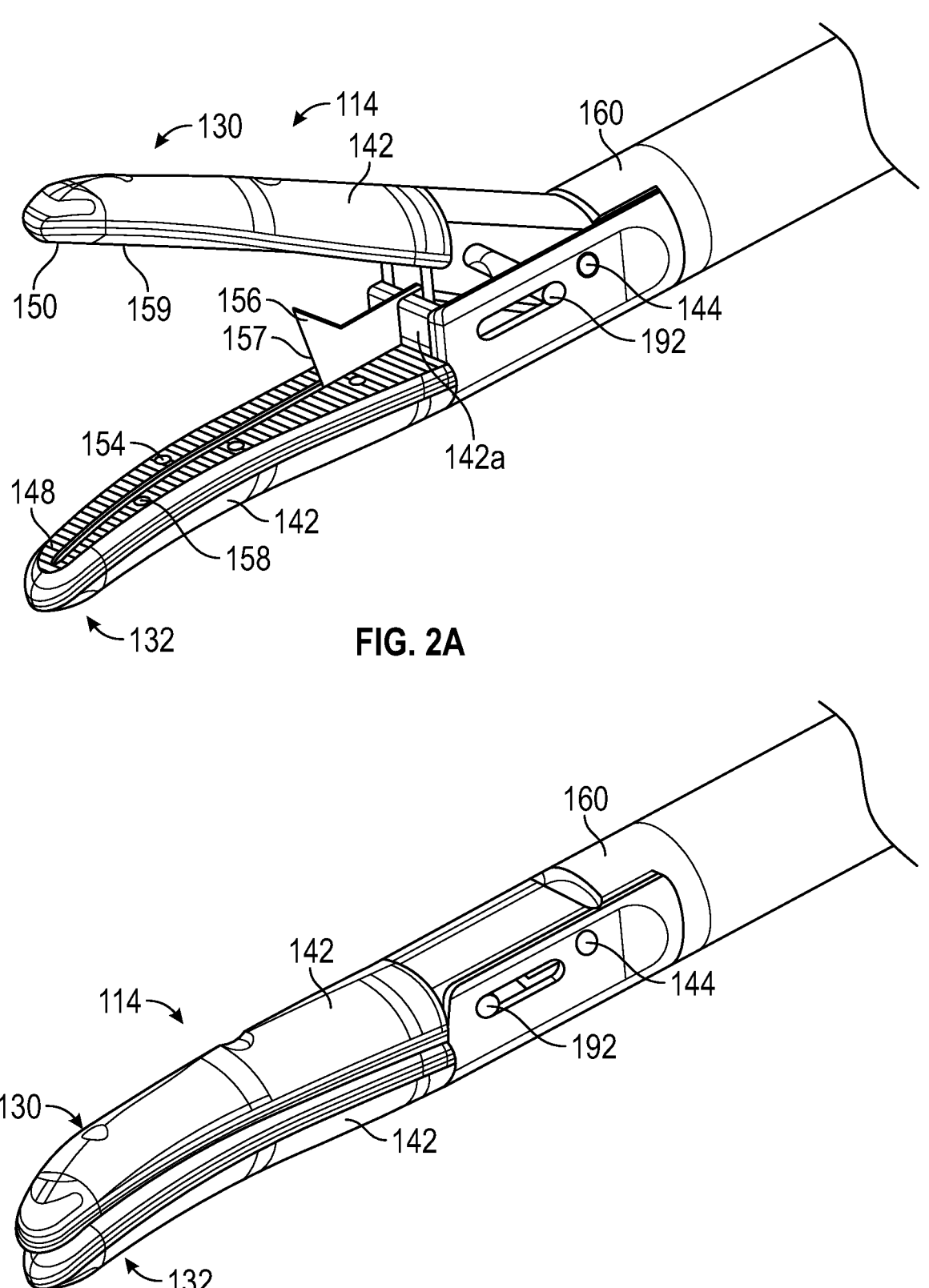
FIG. 2A is an enlarged, perspective view of the end effector of FIG. 1 depicted with a pair of jaw members in an open configuration.
FIG. 2B is an enlarged, perspective view of the end effector of FIG. 1 depicted with the pair of jaw members in a closed configuration.

Referring now to FIGS. 2A-2B, the end effector 114 may be moved from the open configuration (see, e.g., FIG. 2A) wherein tissue (not shown) is received between the jaw members 130, 132, and the closed configuration (see, e.g., FIG. 2B), wherein the tissue is clamped and treated. The jaw members 130, 132 pivot about a pivot pin 144 to move the end effector 114 to the closed configuration of FIG. 2B wherein the sealing plates 148, 150 provide a pressure to tissue grasped therebetween. In some aspects, to provide an effective tissue seal, a pressure within a range between about 3 kg/cm2 to about 16 kg/cm2 and, desirably, within a working range of about 7 kg/cm2 to about 13 kg/cm2, may be applied to the tissue. Also, in the closed configuration, a separation or gap distance is maintained between the sealing plates 148, 150 by an array of stop members 154 (see, e.g., FIG. 2A) disposed on or adjacent the sealing plates 148, 150. The stop members 154 contact opposing surfaces on the opposing jaw member 130, 132 and prohibit further approximation of the sealing plates 148, 150. In some configurations, to provide an effective tissue seal, an appropriate gap distance of about 0.001 inches to about 0.010 inches and, desirably, between about 0.002 inches to about 0.005 inches, may be provided. In some aspects, the stop members 154 are constructed of a heat-resistant ceramic deposited onto the jaw members 130, 132. In other embodiments, the stop members 154 are constructed of an electrically non-conductive plastic molded onto the jaw members 130, 132, e.g., by a process such as overmolding or injection molding. The stop members 154 may define any suitable number, arrangement, and/or configuration, depending on a particular purpose.

Figure 3:
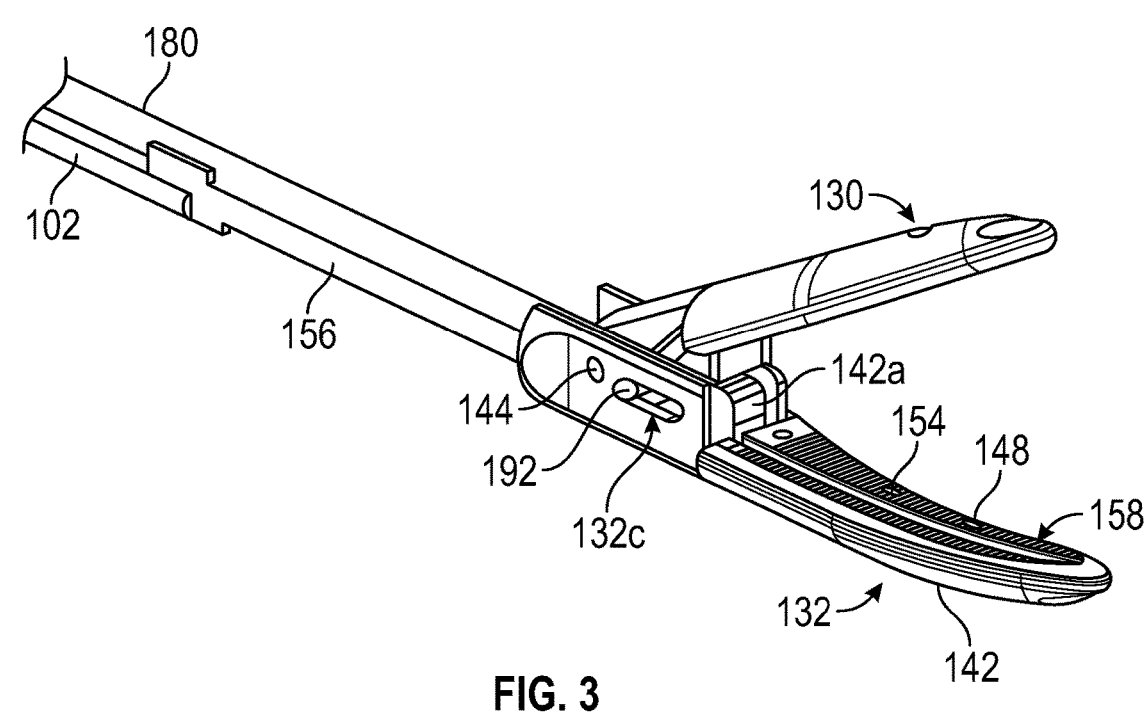
FIG. 3 is a partial, proximal-facing perspective view of a distal portion of a jaw actuation mechanism of the end effector of FIG. 1.

Referring now to FIG. 3, the end effector 114 is shown in the open configuration. Since the inner actuation member 180 is coupled to the cam pin 192, when the outer shaft member 160 (removed from view in FIG. 3 for clarity) is in an unactuated or distal position such that the inner actuation member 180 is in a proximal position relative to the outer shaft member 160, the cam pin 192 is located in a proximal position in cam slots 130c and 132c defined through the flags 130a, 130b, 132a, 132b of the jaw members 130, 132, respectively.

The outer shaft member 160 may be drawn proximally relative to the inner actuation member 180 and the cam pin 192 to move the end effector 114 to the closed configuration (see, e.g., FIG. 2B). Since the longitudinal position of the cam pin 192 is fixed, and since the cam slot 130c is obliquely arranged with respect to the longitudinal axis A-A, proximal retraction of the outer shaft member 160 induces distal translation of the cam pin 192 through the cam slots 130c, 132c such that the jaw member 130 pivots toward jaw member 132 about the pivot pin 144. Conversely, when the end effector 114 is in the closed configuration, longitudinal translation of the outer shaft member 160 in a distal direction induces proximal translation of the cam pin 192 through the cam slots 130c, 132c such that jaw member 130 pivots away from jaw member 132 toward the open configuration.

In some aspects, the inner actuation member 180 may be configured to move relative to the outer shaft member 160 to move the end effector 114 between the open and closed configurations. In this scenario, the moveable handle 122 may be operably coupled to the inner actuation member 180 and the washer 187 coupled to the proximal portion 188 of the inner actuation member 180 may be removed such that the inner shaft member 180 is free to move longitudinally along the longitudinal axis A-A upon actuation of the moveable handle 122. Proximal retraction of the inner actuation member 180 may induce proximal translation of the cam pin 192 through the cam slots 130c, 132c such that the jaw member 130 pivots away from jaw member 132 about the pivot pin 144 toward the open configuration. Conversely, when the end effector 114 is in the open configuration, longitudinal translation of the inner actuation member 180 in a distal direction induces distal translation of the cam pin 192 through the cam slots 130c, 132c such that jaw member 130 pivots toward jaw member 132 toward the closed configuration.

Figure 4:
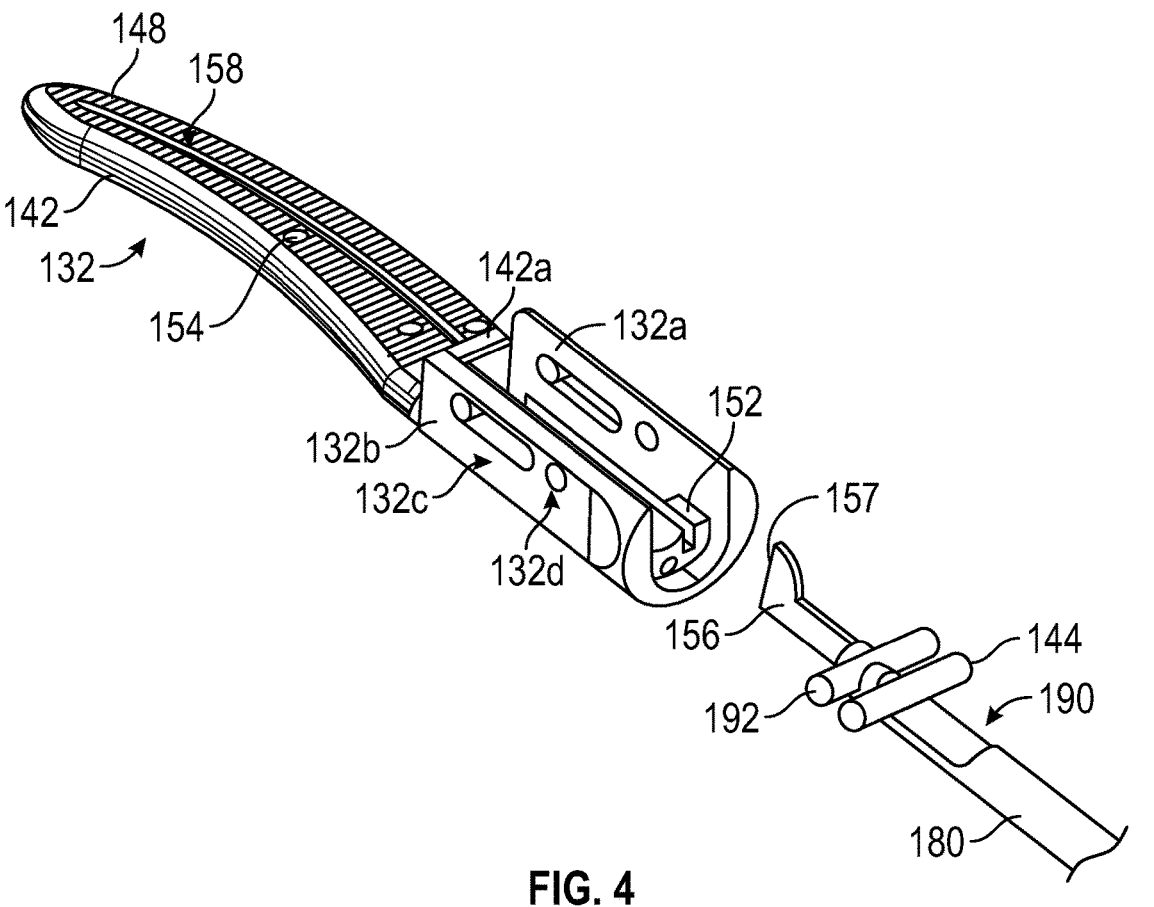
FIG. 4 is a partial, distal-facing perspective view of the distal portion of the jaw actuation mechanism of FIG. 3 and a distal portion of a knife actuation mechanism of the end effector of FIG. 1.

Referring now to FIG. 4, the pins 144, 192 do not interfere with the reciprocal motion of the knife blade 156. A proximal portion of the insulator 142 forms a blade guide 152 that serves to align the knife blade 156 such that the knife blade 156 readily enters the knife channel 158 defined in the jaw members 130, 132 (jaw member 130 removed from view in FIG. 4 for clarity).

Figure 5:
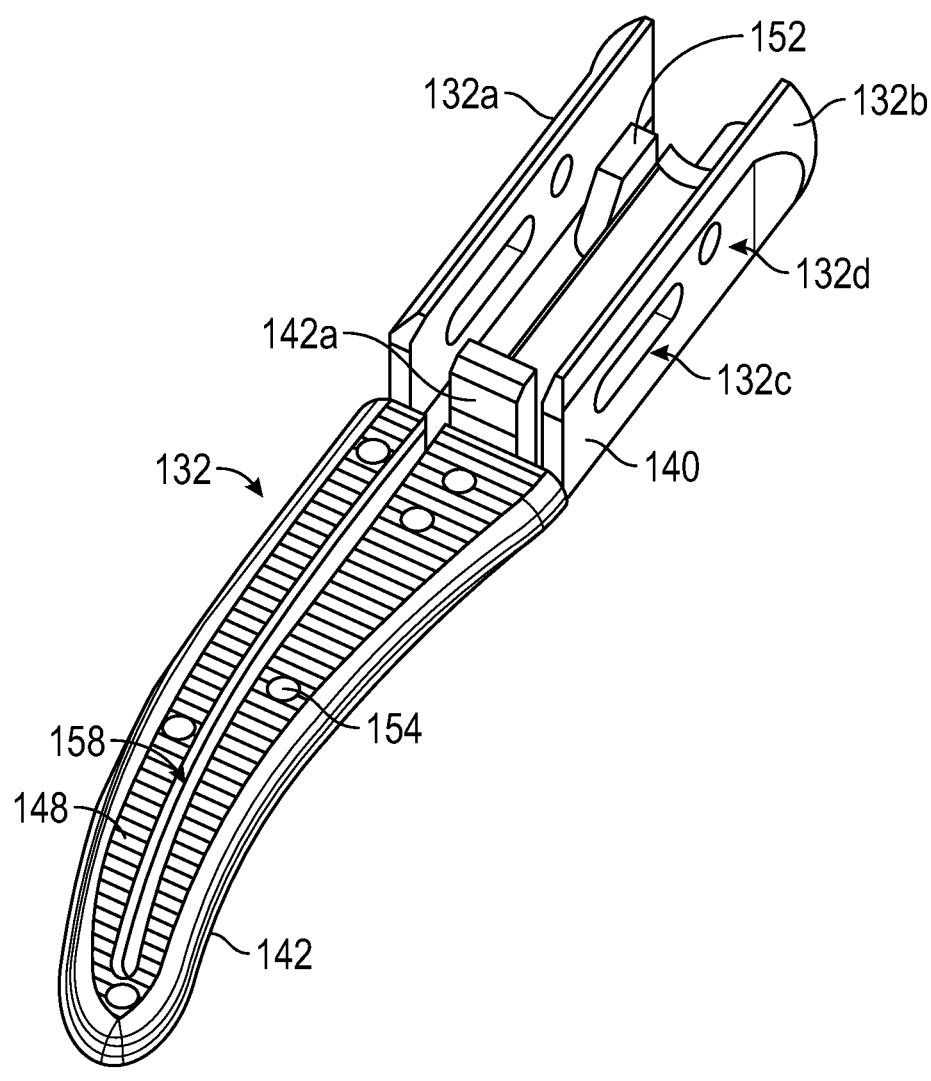
FIG. 5 is a perspective view of a lower jaw member of the end effector of FIG. 1.

Referring now to FIG. 5, the lower jaw member 132 includes, for example, three components: the jaw insert 140, the insulator 142, and the sealing plate 148. The flags 132a, 132b of the jaw member 132 define a proximal portion of the jaw insert 140 and a generally u-shaped profile of the jaw insert 140 extends distally to support the tissue engaging portion of the jaw member 132. Upper jaw member 130 includes the same three major components as lower jaw member 132, including sealing plate 150, jaw insert 140, and insulator 142, and is constructed in the same manner as lower jaw member 132. However, lower jaw member 132 is fixedly engaged, e.g., welded, to outer shaft member 160, while upper jaw member 130 is pivotable relative to lower jaw member 132 and outer shaft member 160 between the open and closed configurations. In order to facilitate alignment of lower jaw member 132 and, more particularly, jaw insert 140 of lower jaw member 132, with outer shaft member 160 during welding (or other suitable fixed engagement), jaw insert 140 and outer shaft member 160 may include complementary alignment features, e.g., a complementary recess (not explicitly shown) defined within jaw insert 140 and a complementary protrusion (not explicitly shown) extending from outer shaft member 160. As an alternative to the unilateral configuration detailed above, both of the upper and lower jaw members 130, 132, respectively, may be pivotable relative to one another and outer shaft member 160, thus defining a bilateral configuration.

The insulator 142 of jaw members 130, 132 may be constructed of an electrically insulative plastic such as a polyphthalamide (PPA) (e.g., Amodel®), polycarbonate (PC), acrylonitrile butadiene styrene (ABS), a blend of PC and ABS, nylon, ceramic, etc. The insulator 142 may be overmolded onto the jaw insert 140 in either a single-shot or a two-shot injection molding process such that each of the sealing plates 148, 150 are coupled to and in spaced relation with their respective jaw inserts 140. Additionally or alternatively, the insulator 142 may be mechanically coupled to the jaw insert 140, e.g., pressed, snapped, glued, etc. Various features may be molded into the insulator 142 that facilitate the attachment of the sealing plates 148, 150 to the jaw inserts 140. For example, tabs may be provided that permit a snap-fit attachment, or ridges may be formed that permit ultrasonic welding of the sealing plates 148, 150 onto the insulators 142. In some configurations, the insulator 142 on the lower jaw member 132 forms a tissue stop 142a extending therefrom adjacent to the knife channel 158 and proximal to the sealing plate 148. The tissue stop 142a serves to prevent tissue from entering the distal end of the outer shaft member 160 and to prevent splay of the flags 130a, 130b of the upper jaw member 130. In some aspects, the tissue stop 142a may be formed by the insulator 142 on the upper jaw member 130 or on both the upper jaw member 130 and the lower jaw member 132. The tissue stop 142a may also serve to align the knife blade 156 as the knife blade 156 enters the knife channel 158 defined in the jaw members 130, 132. To this end, the surface of the tissue stop 142a extending along the path of the knife blade 156 may define a chamfered configuration to further facilitate alignment of the knife blade 156 as the knife blade 156 enters the knife channel 158.

Referring particularly to FIGS. 1, 2A, 2B and 6-8, another tissue sealing plate 648 employable by end effector assembly 114 or the end effector assembly of any other suitable electrosurgical instrument is described. The sealing plate 648 defines a first surface 659 facing the second jaw member (see, e.g., jaw member 130 in FIG. 1). A second sealing plate (e.g., sealing plate 150 in FIG. 2A) is positioned on the second jaw member 130. The second sealing plate 150 defines a second surface 159 (see, e.g., FIG. 2A) facing the first jaw member (e.g., jaw member 132 in FIG. 1). A mesa 660 is formed in the first sealing plate 648. The mesa 660 protrudes from the first surface 659 toward the second surface 159 (see, e.g., FIG. 2A) in the second position (see, e.g., FIG. 2B) of the first and second jaw members 132, 130. The mesa 660 defines a surface substantially parallel to and raised above the first surface 659 of the sealing plate 648. In aspects, the mesa 660 is cylindrical so as to define a surgical surface, although other configurations are also contemplated, e.g., oval, rectangular, polygonal, etc. A material 661 is disposed on the mesa 660. The mesa 660 and the material 661 define a stop member 654. The stop member 654 maintains a gap distance between the first and second surfaces 659, 159 when the first and second jaw members 132, 130 are in the second position.

In some aspects, the material 661 of stop member 654 is a heat-resistant ceramic deposited onto the mesa 660. The heat-resistant ceramic material may be electrically non-conductive. In other aspects, the material 661 is an electrically non-conductive plastic molded onto the mesa 660 (e.g., by injection molding). Other materials (single materials or plural materials), both conductive, non-conductive, or combinations thereof are also contemplated. Plural stop members 654 may be provided and may define any suitable number, arrangement, and/or configuration, depending on a particular purpose. Where multiple stop members 654 are provided, such may be similar or different from one another, e.g., in height, diameter, material, shape, etc. As an example, the height of an extruded mesa may be different based on the diameter of the mesa. For example, a smaller dot mesa may be taller than a larger diameter one on the same sealplate to achieve the same stop member height target.

According to aspects of the disclosure, the material 661 disposed on the mesa 660 is deposited onto the mesa 660 as a fluid which is then hardened to form an upper portion of the stop member 654.

Figure 6:
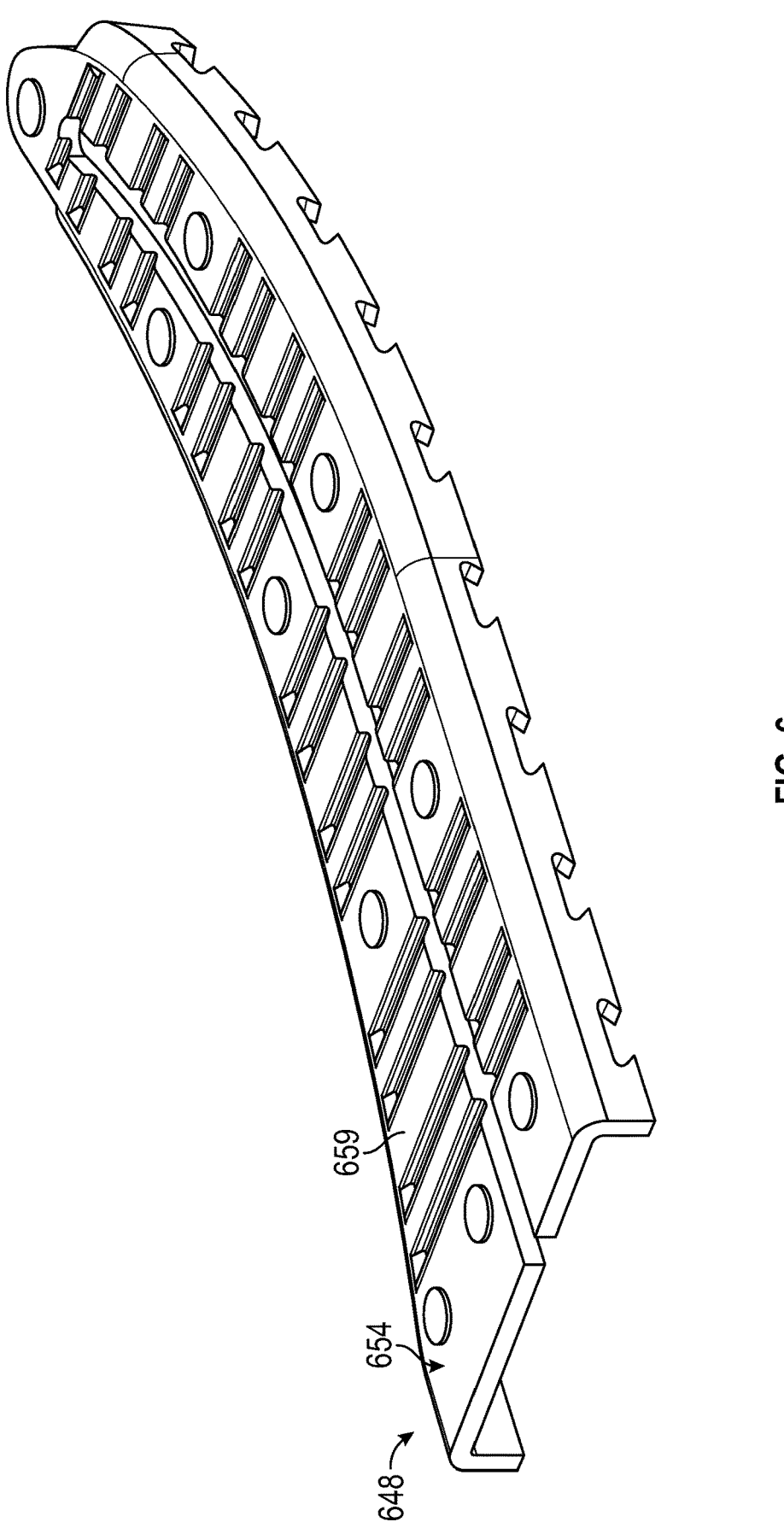
FIG. 6 is a perspective view of another tissue sealing plate configured for use with the end effector of FIG. 1.
Figure 7:
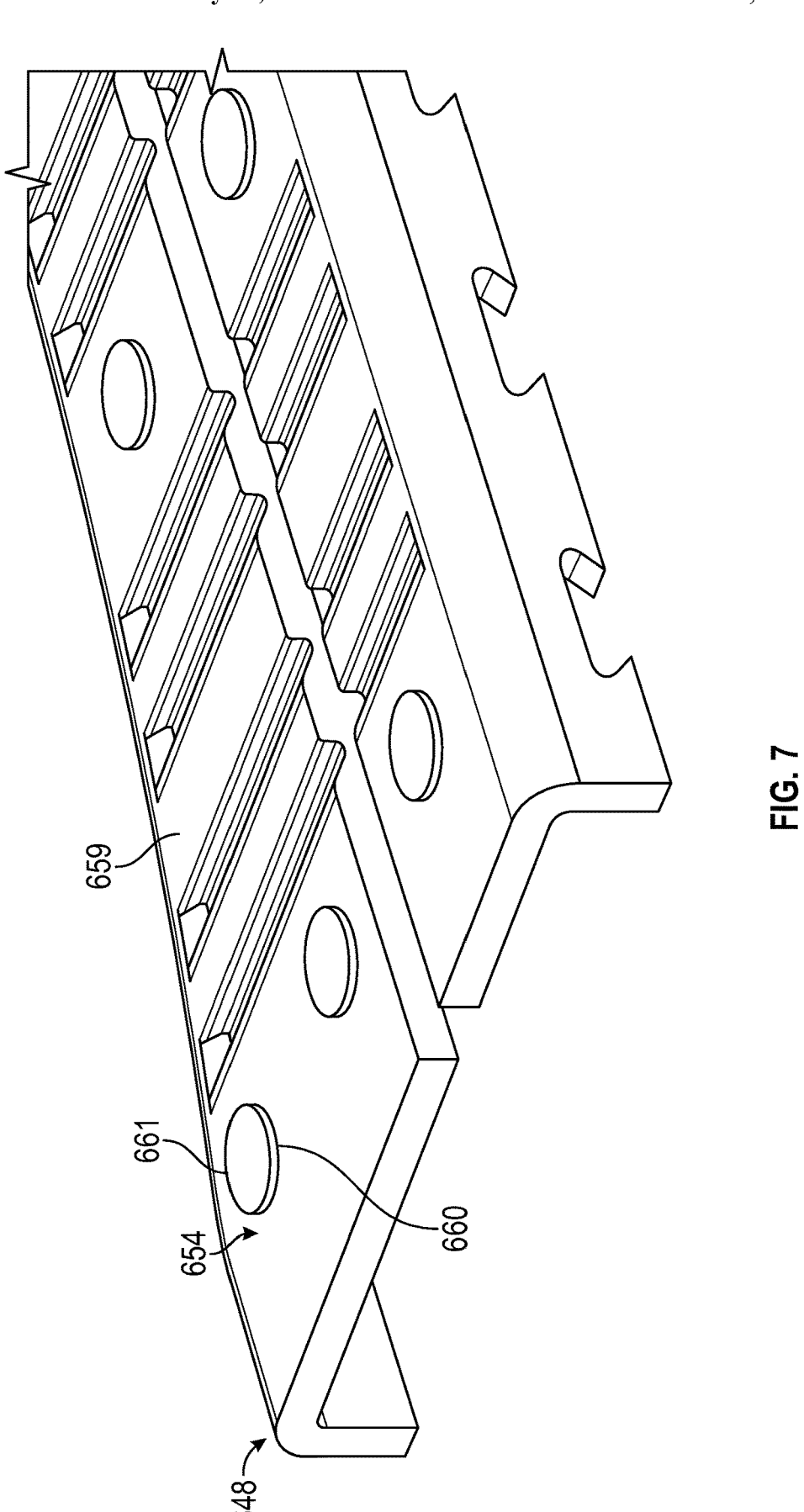
FIG. 7 is an enlarged, perspective view of the tissue sealing plate of FIG. 6.
Figure 8:
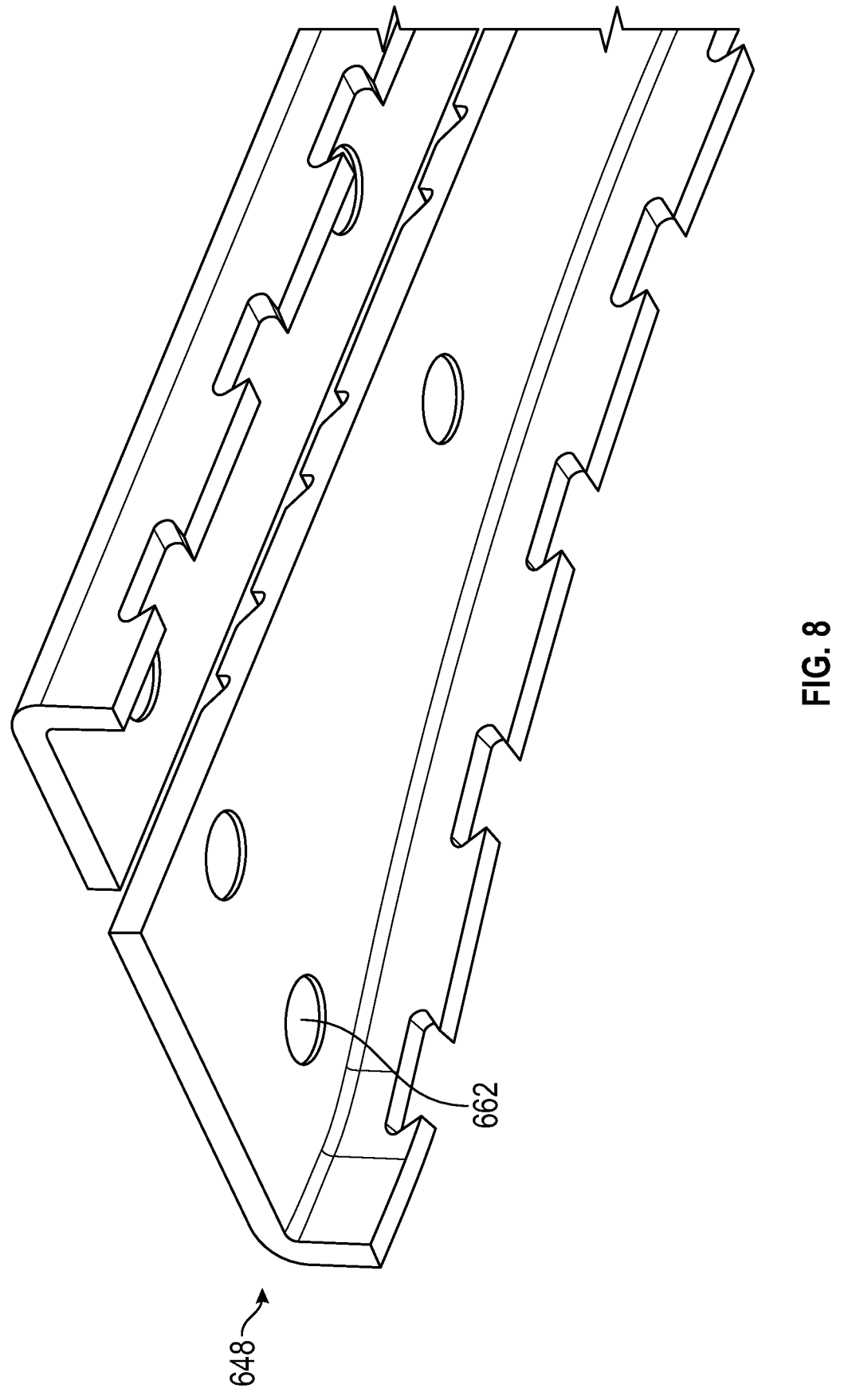
FIG. 8 is a bottom, enlarged, perspective view of the tissue sealing plate of FIG. 7.

Referring particularly to FIGS. 6-8, the material 661 on the mesa 660 is spaced apart from the first surface 659 of the sealing plate 648. That is, the material 661 does not contact the first surface 659 of the tissue sealing plate 648. This may be achieved by deposition of a volume of material 661 onto the mesa 660 such that the material 661 does not overflow or run off onto the first surface 659.

A diameter (or width) of the material 661 on the mesa 660 may be substantially the same as a diameter (or width) of the surface of the mesa 660 facing away from the first surface 659. Alternatively, the diameter (or width) of the material on the mesa 660 may be smaller than the diameter (or width) of the surface of the mesa 660 facing away from the first surface 659.

In some aspects, the material 661 on the mesa 660 defines a dome shape having a relatively wider base closer to the first surface 659 and a curved surface facing away from the first surface 659.

Referring particularly to FIG. 8, an indent 662 may result from the formation of each raised mesa 660. The mesas 660 may be formed in this manner by stamping, either together with the formation of tissue sealing plate 648 or subsequent thereto.

While tissue sealing plate 648 is described as employable in jaw member 132, a similar tissue sealing plate may additionally or alternatively be employed in jaw member 130. For example, tissue sealing plate 648 may be employed in jaw member 132 and another tissue sealing plate having a mirror image of tissue sealing plate 648 may be employed in jaw member 130.

While several aspects of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. An end effector assembly for a surgical instrument, comprising:

a pair of opposing first and second jaw members operably coupled with each other such that at least one of the first or second jaw members is movable relative to the other of the first or second jaw members from a first position wherein the first and second jaw members are disposed in spaced relation relative to one another to a second position wherein the first and second jaw members cooperate to grasp tissue therebetween;

a first sealing plate positioned on the first jaw member, the first sealing plate defining a first surface facing the second jaw member;

a second sealing plate positioned on the second jaw member, the second sealing plate defining a second surface facing the first jaw member;

a mesa formed in the first sealing plate and having a top surface spaced from the first surface, the mesa protruding from the first surface toward the second surface in the second position of the first and second jaw members; and a material disposed on the top surface of the mesa by depositing fluid onto the top surface and hardening the fluid, wherein the material is separated from the first surface by the mesa and at least partially defines a stop member, the stop member configured to maintain a gap distance between the first and second surfaces when the first and second jaw members are in the second position.

2. The end effector assembly of claim 1, wherein the first surface of the first sealing plate or the second surface of the second sealing plate is an electrically conductive tissue sealing surface.

3. The end effector assembly of claim 1, further including a knife and knife channel defined in at least one of the first or second jaw members, the knife longitudinally extendable within the knife channel.

4. The end effector assembly of claim 1, wherein each of the first and second jaw members further includes a jaw insert and an insulator configured to electrically insulate the first and second sealing plates from the jaw inserts of the first and second jaw members.

5. The end effector assembly of claim 1, wherein the material includes a heat-resistant ceramic material.

6. The end effector assembly of claim 1, wherein the material includes an electrically non-conductive plastic.

7. The end effector assembly of claim 1, wherein the gap distance is from about 0.001 inches to about 0.010 inches.

8. The end effector assembly of claim 1, wherein at least one of the first or second jaw members includes an insulator coupled thereto, the insulator configured to electrically insulate the first sealing plate from the first jaw member, or the second sealing plate from the second jaw member.

9. The end effector assembly of claim 8, further including a knife and a knife channel, wherein the insulator is configured to guide the knife into the knife channel.

10. The end effector assembly of claim 1, wherein the material disposed on the mesa defines a dome shape.

* * * * *